United States Patent [19]

Saukaitis

[11] Patent Number: 5,466,808
[45] Date of Patent: * Nov. 14, 1995

[54] 8-SULFO-3-QUINOLINE CARBOXYLIC ACIDS AND PROCESS THEREFORE

[75] Inventor: John C. Saukaitis, East Greenwich, R.I.

[73] Assignee: Hoechst Celanese Corporation, Somerville, N.J.

[*] Notice: The portion of the term of this patent subsequent to Jul. 4, 2012, has been disclaimed.

[21] Appl. No.: 288,374

[22] Filed: Aug. 10, 1994

Related U.S. Application Data

[63] Continuation-in-part of PCT/US94/02100, Feb. 14, 1994, which is a continuation-in-part of Ser. No. 180,593, Jan. 13, 1994, Pat. No. 5,430,152, which is a continuation-in-part of Ser. No. 17,583, Feb. 16, 1993, abandoned.

[51] Int. Cl.$^6$ ................................................ C07D 215/233
[52] U.S. Cl. ................................................................ 546/153
[58] Field of Search ............................................... 546/153

[56] References Cited

U.S. PATENT DOCUMENTS

| | | | |
|---|---|---|---|
| 3,149,104 | 9/1964 | Lesher et al. | 546/123 |
| 3,673,193 | 6/1972 | Lesher et al. | 546/123 |
| 4,528,287 | 7/1985 | Itoh et al. | 514/254 |

OTHER PUBLICATIONS

Hui–Yuan et al, Pharmaceutical Industry, 1986, pp. 390–394.
Bridges et al. J. Heterocyclic Chem, vol. 27, 1990, pp. 1527–1536.

*Primary Examiner*—C. Warren Ivy
*Assistant Examiner*—Zinna N. Davis
*Attorney, Agent, or Firm*—Hugh C. Crall

[57] ABSTRACT

This invention is a process for preparing 8-sulfo-7-chloro-6-fluoro-4-oxo-1,4-dihydro-3-quinolinic acid wherein the amino analinomethylenomalonate starting material of Formula 1 is unsubstituted at the $R_1$ and $R_2$ positions i.e. these moieties are hydrogen. In the ring closing process when $R_1$ and $R_2$ are hydrogen, not only does the ring close but the ring position at $R_2$ is sulfonated.

6 Claims, No Drawings

8-SULFO-3-QUINOLINE CARBOXYLIC ACIDS AND PROCESS THEREFORE

CROSS-REFERENCE TO RELATED APPLICATIONS

This application is a continuation-in-part of PCT Patent Application No. PCT/US94/02100 filed Feb. 14, 1994, which is a continuation-in-part of U.S. patent application Ser. No. 08/180,593 filed Jan. 13, 1994, now U.S. Pat. No. 5,430,152, which is a continuation-in-part of U.S. patent application Ser. No. 08/017,583 filed Feb. 16, 1993, now abandoned.

BACKGROUND OF THE INVENTION

1. Technical Field

The invention relates a new method for to the preparation of 8-sulfo-3-quinolinic carboxylic acids and compositions therefrom.

2. Background

Heterocyclic compounds of the quinolinic acids are known from the literature. They are intermediates for a broad class of compounds known as quinolones which have antibacterial activity. These compounds were prepared in the late 1930's and the early 1940's by the method of R. G. Gould and W. A. Jacobs, J. Amer. Chem. Soc. 61, 2890 (1939). The method consists of the cyclization of diethyl anilinomethylenemalonate derivatives in Dowtherm A, diphenylether at temperatures of 250°–300° C. The starting materials for the cyclization reaction are prepared from a substituted aniline and diethyl ethoxymethylenemalonate. This method has been employed in a number of syntheses, 4,7-Dichloroquinoline, J. Amer. Chem. Soc. 68, 113 (1946); J. Amer. Chem. Soc. 68, 1204 (1946). 6,7 or 8 halo-4-hydroxyquinoline is described in J. Med. Chemistry 21, 268 (1978). Other high boiling solvents have been utilized in this reaction as described in German Offenlegungsschrift Nos. 2,343,462 and 2,441,747, U.S. Pat. Nos. 3,149,104 and 3,673,193 and J. Heterocyclic Chem. 21, 673 (1984). The use of polyphosphoric acid, sulfuric and acetic acid has been described in J. Org. Chem. Soc. 32, 4155 (1967) and 33, 1218 (1968) and J. Heterocyclic Chem. 27, 1527 (1990). In Pharmaceutical Industry 1986, 17 (9) 390– 394, the ring closure of the anilinomethylenemalonate derivative is carried out with various Lewis Acid catalysts namely polyphosphoric ester, polyphosphoric acid, phosphorousoxychloride, phosphorous pentoxide, and a mixture of acetic anhydride and sulfuric acid. The yields obtained with these prior art methods are generally inferior to those of this invention.

A variation on this reaction is the use of anilinomethylenemeldrum's acid esters in place of the normal anilinomethylenemalonic acid esters. These materials are more reactive. However, they are much more expensive to make. Examples of the use of these compounds are given in G.B. Patent 1,147,760; J. Prakt. Chemie. 333, 267 (1990) and J. Heterocyclic Chem. 27, 1527 (1990).

Chloroquine is a quinoline derivative that was found safe for the treatment of plasmodium falciparum malaria in 1946. It was prepared from m-chloroaniline and ethyloxalacetate. The resultant m-chloroanilinomaleate or fumarate derivative was cyclized in diphenylether at high temperature. An industrial procedure is described in Ind. & Eng. Chem (41), 4, 1949, 654–662.

It is advantageous to have a method of preparation that does not utilize Dowtherm A, diphenylether. It is a suspect carcinogen and toxic. High boiling solvents are difficult to separate from the product and generally washing with a low boiling solvent is required to remove the high boiling solvent. In some cases, the addition of a low boiling hydrocarbon solvent is also necessary to precipitate the product from the diphenyl-ether reaction solvent. This situation creates further problems. It is more difficult to recycle the solvent under these conditions. It is advantageous to carry out the reaction in a solvent that can be diluted with water and disposed of without presenting an environmental hazard. It is also an advantage to use inexpensive, readily available starting materials. These and other advantages are achieved by the invention.

Although polyphosphoric, sulfuric, and acetic acid have been found to be effective reaction solvents for the cyclization of certain halogen substituted anilinomethylenemalonates as noted above, they do not generally provide the high yields of this invention. The present invention provides an efficient process for preparation of novel 8-sulfo-3-quinolinic acids in high yield by the cyclization and sulfonation of anilinoacrylic acid esters selected from anilinomethylenemalonate, anilinofumurate and anilinomaleate thereof at a moderate temperature without the use of environmentally dangerous, toxic solvents.

SUMMARY OF THE INVENTION

This invention is directed to 8-sulfo-3-quinolinic acids and a process for their preparation by the cyclization of anilinomethylenemalonate, anilinofumurate and anilinomaleate esters in a reaction medium comprising chlorosulfonic acid or fuming sulfuric acid (oleum) and mixtures thereof. The cyclization and sulfonation of phenylamino esters takes place with surprising and unexpected ease in the presence of chlorosulfonic acid or fuming sulfuric acid (oleum).

The process of the invention is illustrated below:

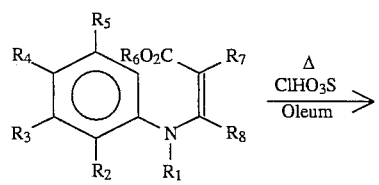

Formula 1

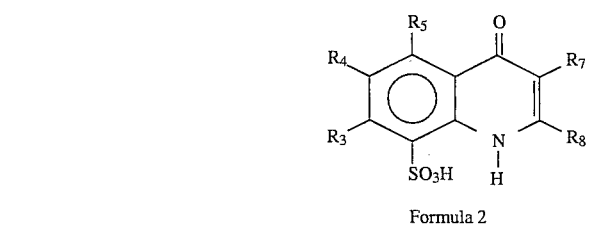

Formula 2

The substituents in the above formulas have the following meanings:

$R_1$ and $R_2$ is hydrogen;

$R_3$ is hydrogen or chloro;

$R_4$ is hydrogen, F or Cl, preferably $R_4$ is fluorine;

$R_5$ is hydrogen, F, Cl, Br, I, $C_1$-$C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and n=2;

$R_6$ is hydrogen, $C_1$-$C_5$ alkyl, $C_3$-$C_6$ cyclo alkyl or phenyl;

$R_7$ is hydrogen, $C_1$-$C_5$ alkyl, alkoxycarbonyl wherein said alkoxy portion is a $C_1$-$C_5$ alkoxy or a $C_2$-$C_6$ cycloalkoxy, a phenoxycarbonyl; and $R_8$ is hydrogen, $C_1$-$C_5$ alkyl, alkoxycarbonyl, as defined above or phenoxycarbonyl which may be substituted with a halogen or alkyl.

The compositions of the invention may be represent by compounds of Formula 2 wherein $R_7$ is carboxyl.

In the process of the invention, the reaction medium comprises chlorosulfonic acid, fuming sulfuric acid (oleum) and mixtures thereof. Fuming sulfuric acid or oleum is a solution of sulfur trioxide in concentrated sulfuric acid. An oleum reaction medium containing 5–30% sulfur trioxide provided excellent results. The reaction medium may be used in an amount equal to about 2 to 10 times the weight of the Formula 1 reactant. The process may be conducted at a temperature of about 40°–180° C., more preferably about 60°–150° C., and most preferably about 70°–90° C.

DESCRIPTION OF THE PREFERRED EMBODIMENTS

This invention is directed to substituted 8-sulfo-1,4-dihydro-4-oxo-3-quinolinic acids and a method for their preparation which comprises heating an ester selected from the group consisting of substituted anilinomethylenemalonates, anilinofumarates and anilinomaleates in the presence of chlorosulfonic acid or fuming sulfuric acid (oleum) and mixtures thereof. The invention provides an efficient environmentally safe process for preparing quinolinic acids in high yield under moderate reaction conditions. These phenylamino esters may be depicted by the following general formula:

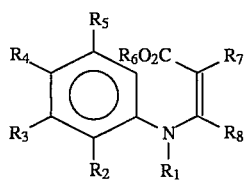

Formula 1

The substituents in the above formulas have the following meanings:

$R_1$ and $R_2$ are hydrogen;

$R_3$ is hydrogen, Cl, F, preferably Cl;

$R_4$ is hydrogen, F or Cl, preferably $R_4$ is fluorine;

$R_5$ is hydrogen, F, Cl, Br, I, $C_1$-$C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and n=2;

$R_6$ is hydrogen, $C_1$-$C_5$ alkyl, $C_3$-$C_6$ cycloalkyl or phenyl;

$R_7$ is hydrogen, $C_1$-$C_5$ alkyl, alkoxycarbonyl wherein said alkoxy portion is a $C_1$-$C_5$ alkoxy or a $C_2$-$C_6$ cycloalkoxy or, a phenoxycarbonyl; and $R_8$ is hydrogen or $C_1$-$C_5$ alkyl.

The anilinomethylenemalonate, anilinofumarate and anilinomaleate starting materials may be prepared by known methods; e.g. by the condensation of m-chloroaniline and ethyloxalacetate to produce m-chloroanilinomaleate or fumarate (Ind. & Eng. Chem (41) 4, 1949, 654–662) and by the condensation of a substituted or unsubstituted aniline with diethyl ethoxy-methylenemalonate to produce diethyl anilinomethylenemalonate (J. Amer. Chem. Soc. 68, 113 (1946)).

Exemplary esters are:
diethyl-3-chloro-4,5-difluoroanilinomethylenemalonate;
diethyl-3-chloro-4-fluoroanilinomethylenemalonate;
diethyl-3-chloro-4-fluoroanilinofumurate; and
diethyl-3-chloro-4-fluoroanilinomaleate;

Compounds of the general Formula 1 are cyclized and sulfonated in a chlorosulfonic acid or an oleum reaction medium to yield substituted 8-sulfo-3-quinolinic acids and derivatives thereof having the following general Formula 2:

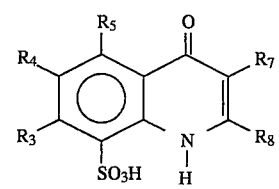

Formula 2

The substituents $R_1$-$R_8$ are defined above with the alcohol, $R_6OH$ being eliminated in the cyclization reaction. The moiety $R_7$ in the ester form is hydrolyzed to the acid form by drowning the reaction mixture. A mixed reaction medium comprising chlorosulfonic acid and oleum may be employed in the cyclization reaction.

The ring closure reaction is conducted at a temperature from about 40°–180° C., more preferably about 60°–150° C., most preferably about 70°–90° C. In a preferred embodiment the reaction is conducted at 80° C. The starting material (uncyclized compounds of Formula 1) is heated in a reaction medium comprising chlorosulfonic acid; or fuming sulfuric acid, and mixtures thereof. Optionally a diluent may be present such as nitric acid, phosphoric acid or sulfuric acid or an organic solvent such as acetic acid, acetic anhydride propanoic acid or dichlorobenzene and mixtures thereof. The reaction medium is preferably undiluted chlorosulfonic acid or undiluted oleum. The ratio of chlorosulfonic acid or oleum to the starting material (Formula 1 compound) may be in the range of 2:1 to 10:1. The reaction time will depend upon the ease with which the ring closure is effected. Generally the reaction is carried out over a period of about 5 minutes to about 6 hours, preferably about 0.5 to about 3 hours. The term, "oleum" or "fuming sulfuric acid" as used in this specification is intended to mean a solution of sulfur trioxide in concentrated sulfuric acid. Oleum is a common reagent in the chemical industry being readily available in sulfur trioxide concentrations ranging from 5 to 30 percent.

An appropriate reaction time can be determined by simple experimentation. After completion of the reaction period, the desired quinolinic acid may be recovered by simply drowning the reaction mixture in ice water in a weight ratio of 10:1 to 3:1 (water to acid) preferably about 4:1 and filtering the resultant slurry.

The process of the invention may be advantageously used to prepare fluorosubstituted quinoline carboxylic acids which are useful intermediates for the preparation fluorinated quinolone antibacterial compounds (see for example U.S. Pat. No. 4,528,287). Exemplary intermediates which can be prepared according to this invention are:

1,4-dihydro-4-oxo-5,6 difluoro-7-chloro-8-sulfo-3-quinolinic acid;

1,4-dihydro-4-oxo-5-methyl-6-fluoro-7-chloro-8-sulfo-3-quinolinic acid;

1,4-dihydro-4-oxo-5,6-difluoro-7-chloro-8-sulfo-3-quinolinic acids;

The following example illustrate the invention. This example is illustrative and not intended to limit the scope of the invention.

EXAMPLES

Example 1

This example illustrates a process for preparing 8-sulfo-7-chloro-6-fluoro-4-oxo-1,4-dihydro-3-quinolinic acid wherein the anilinomethylenemalonate starting material of Formula 1 is unsubstituted at the $R_1$ and $R_2$ positions i.e. these moieties are hydrogen. In the ring closing process when $R_1$ and $R_2$ are hydrogen, not only does the ring close but the ring position at $R_2$ is sulfonated.

100 grams of diethyl-3-chloro-4-fluoranilinomethylenemalonate was added to 400 grams of 20% oleum maintaining the temperature in a range of 70°–80° C. When the addition was complete, the reaction mixture was heated at 80° C. for 4 hours. The reaction was allowed to cool to room temperature and was drown into 1000 grams of ice. The solid was filtered. The solid cake was washed with 3 100 ml portions of ice cold methanol. The wet cake was dried in a vacuum oven overnight at 60° C. and 62.3 g of 8-sulfo-7-chloro-6-fluoro-4-oxo-1,4-dihydro-3-quinolinic acid was obtained in 61.2% Yield, 99% assay. The structure was verified by both I.R. and N.M.R.

The invention also may be conducted in a continuous or batch method and may be embodied in other specific forms without departing from the spirit or essential characteristics thereof. Through this specification and the appended claims, a given chemical name or formula is intended encompass all isomers of said name or formula where such isomers exist. The present embodiments are therefore to be considered in all respects as illustrative and not restrictive, the scope of the invention being indicated by the appended claims rather than by the foregoing description; and all changes which come within the meaning and equivalency of the claims are therefore intended to be embraced therein.

I claim:

1. A method for preparing an 8-sulfo-3-quinolinic carboxylic acid and derivatives thereof which comprises heating an ester in a reaction medium selected from chlorosulfonic acid, oleum and mixtures thereof wherein said ester has the following formula:

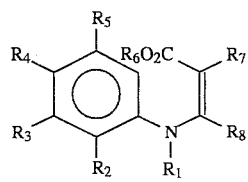

wherein:

$R_1$ and $R_2$ are hydrogen;

$R_3$ is hydrogen or chloro;

$R_4$ is hydrogen, chloro or fluoro;

$R_5$ is hydrogen, F, Cl, B, I, $C_1$-$C_5$ alkyl, a halogen substituted $C_1$ to $C_5$ alkyl, $C_1$ to $C_5$ alkoxy, $NO_2$—, $R_nN$— wherein R is independently hydrogen or $C_1$ to $C_5$ alkyl and n=2;

$R_6$ is hydrogen, $C_1$-$C_5$ alkyl, $C_3$-$C_6$ cyclo alkyl or phenyl;

$R_7$ is hydrogen, $C_1$-$C_5$ alkyl, alkoxycarbonyl wherein said alkoxy portion is a $C_1$-$C_5$ alkoxy or a $C_2$-$C_6$ cycloalkoxy, a phenoxycarbonyl; and $R_8$ is hydrogen or $C_1$-$C_5$ alkyl.

2. A method according to claim 1 wherein said ester has the following formula:

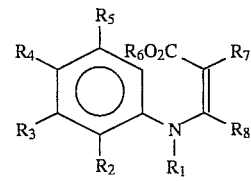

wherein:

$R_1$ and $R_2$ are hydrogen;

$R_3$ is Cl;

$R_4$ is F;

$R_5$ is hydrogen, F, Cl, $C_1$-$C_5$ alkyl, $C_1$- to $C_5$ alkoxy or $NO_2$—;

$R_6$ is hydrogen, $C_1$-$C_5$ alkyl, $C_3$-$C_6$ cyclo alkyl or phenyl;

$R_7$ is alkoxycarbonyl wherein said alkoxy portion is a $C_1$-$C_5$ alkoxy or a $C_2$-$C_6$ cycloalkoxy or, a phenoxycarbonyl; and $R_8$ is hydrogen or $C_1$-$C_5$ alkyl.

3. A method according to claim 1 wherein said heating is conducted at a temperature of about 40°–180° C.

4. A method according to claim 1 wherein said heating is conducted at a temperature of about 60°–150° C.

5. A method according to claim 1 wherein said heating is conducted at a temperature of about 70°–90° C.

6. A method according to claim 1 wherein said reaction medium contains a diluent.

* * * * *